United States Patent [19]

Skorianetz et al.

[11] 4,123,394

[45] Oct. 31, 1978

[54] TRICYCLO[5.2.1.0$^{2,6}$]DECANE-METHYLOL OR ITS LOWER ALKYL OR ALKENYL ESTER OR ETHER DERIVATIVES IN PERFUME COMPOSITIONS

[75] Inventors: Werner Skorianetz, Dardagny; Khurshid P. Dastur, Satigny; Hugo Strickler, Dardagny, all of Switzerland

[73] Assignee: Firmenich SA, Geneva, Switzerland

[21] Appl. No.: 746,211

[22] Filed: Dec. 1, 1976

[30] Foreign Application Priority Data

Dec. 8, 1975 [CH] Switzerland ................ 15897/75

[51] Int. Cl.$^2$ ............................................. C11B 9/00
[52] U.S. Cl. ............................... 252/522; 252/89 R; 568/817
[58] Field of Search ............................................. 252/522

[56] References Cited

U.S. PATENT DOCUMENTS

3,271,259  9/1966  Saunders ........................ 252/522

FOREIGN PATENT DOCUMENTS

2,307,627  9/1974  Fed. Rep. of Germany ........... 252/522

*Primary Examiner*—Veronica O'Keefe
*Attorney, Agent, or Firm*—Pennie & Edmonds

[57] ABSTRACT

Processes and compositions are described for improving, enhancing and modifying the fragrance of products including perfumes, perfume compositions and perfumed articles utilizing as effective ingredients tricyclo[5.2.1.0$^{2,6}$]decane-methylol or one of its lower alkyl or alkenyl ester or ether derivatives.

8 Claims, No Drawings

TRICYCLO[5.2.1.0$^{2,6}$]DECANE-METHYLOL OR ITS LOWER ALKYL OR ALKENYL ESTER OR ETHER DERIVATIVES IN PERFUME COMPOSITIONS

BACKGROUND OF THE INVENTION

Various tricyclodecane derivatives have been described as being useful in modifying the fragrance properties of perfumes and perfumed articles:

(a) German Patent Application No. 2,307,627 teaches, for example, that the diol of formula

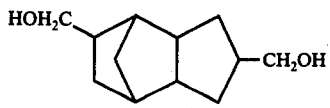

possesses an elegant and long-lasting musk odour.

(b) The aldehyde derivative of formula

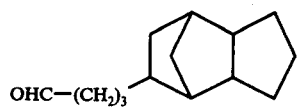

has been described in German Patent Application No. 2,359,659 as an ingredient able to confer a lily-of-the-valley and honeysuckle tonality.

(c) German Patent Application No. 2,006,388 describes the aldehyde of formula

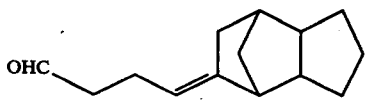

This compound is characterized by its green, flowery and lily-of-the-valley odour.

(d) German Auslegeschrift No. 1,218,643 defines the odours of compounds

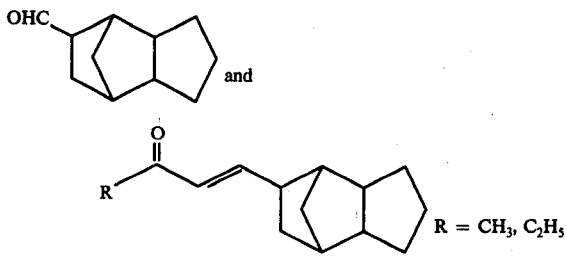

as being reminiscent of those developed by dried wood with a winey topnote or an iris-like fragrance.

(e) U.S. Pat. No. 3,271,259 teaches the utility of the ester of formula

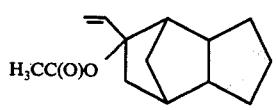

for developing a lavender scent.

With the exception of the first of the above-mentioned compounds - see reference a) above - all the said known tricyclic derivatives show a substitution exclusively on the cyclohexanic ring. None of them, however, possesses a fragrance analogous, in terms of both quality and lasting power effect, to that developed by the compounds of the invention.

Tricyclo[5.2.1.0$^{2,6}$]decane methylol and some of its ester derivatives are known compounds whose utility, however, was confined to the industry of softeners and lubricating oils — see in particular German Patent No. 934,889.

THE INVENTION

It has now been surprisingly discovered that the said tricyclo[5.2.1.0$^{2,6}$]decane-methylol and its esters or ethers of formula

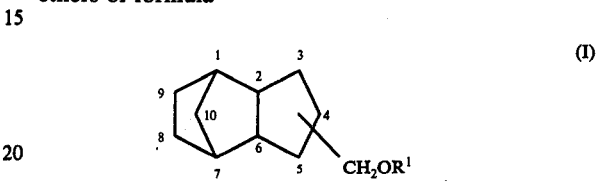

wherein symbol $R^1$ represents a lower saturated or unsaturated, linear or branched alkyl radical, having from 1 to 6 carbon atoms, an acyl radical containing from 1 to 6 carbon atoms or a hydrogen atom, and wherein the side-chain is bound to the cyclopentane ring at positions 4 or 5 of the said ring, possess very useful perfuming properties and consequently can be used advantageously for improving, enhancing or modifying the fragrance character of perfumes, perfume compositions and perfumed articles.

The present invention relates therefore to a process for preparing perfumes, perfume compositions and perfumed articles comprising the step of admixing a fragrance-imparting amount of a compound of formula (I) together with other perfuming coingredients, carriers or diluents.

This invention provides further a perfumed article comprising having added thereto as fragrant ingredient a compound of formula (I).

The present invention relates further to a perfume composition comprising a fragrance-modifying amount of a compound of formula (I).

In formula (I) given above, substituent $R^1$ can represent a lower alkyl or alkenyl radical such as, for example, a methyl, ethyl, propyl, isopropyl, butyl, ter-butyl, amyl, isoamyl, sec-amyl, allyl or but-2-enyl radical.

When substituent $R^1$ stands for an acyl radical, it is deemed to preferentially define a formyl, acetyl, propionyl, butyryl or an isobutyryl group. Compounds (I) develop various odoriferous notes ranging from flowering or fruity to woody notes. These fragrance characters are particularly suitable for perfuming a wide range of products. Thus, the compounds of the invention favourably develop the scent of fine perfume compositions as well as that of cosmetics, talc powders, bath preparations, shampoos, hair lotions, shaving creams, soaps, detergents or household materials such as waxes or air-fresheners.

The proportions at which the above compounds of formula (I) can promote favourable perfuming effects in accordance with the invention vary within a wide range. Preferential concentrations are comprised between about 0.5 and 5% by weight of the compounds of the invention based on the total weight of the composition into which they are incorporated. The said amounts are suitable to confer to the thus-obtained compositions a pleasant and well-balanced olfactive harmony.

It will be appreciated by those skilled in the art that the proportions indicated may rise beyond the given upper limit in accordance with the specific need it is desired to fulfil, so that concentrations of up to 25 or even 50% by weight of the compounds of the invention can be suitably employed for the preparation of perfume concentrates or perfume "coeurs".

The compounds of formula (I) can be used alone or in admixture with other perfuming coingredients, or inert vehicles such as carriers, solvents or diluents.

The compounds of formula (I) include, inter alia, the following compounds of particular utility:

tricyclo[5.2.1.0$^{2,6}$]decane-methylol,
tricyclo[5.2.1.0$^{2,6}$]dec-4-yl-methyl and tricyclo[5.2.1.0$^{2,6}$]dec-5-yl-methyl formate,
tricyclo[5.2.1.0$^{2,6}$]dec-4-yl-methyl and tricyclo[5.2.1.0$^{2,6}$]dec-5-yl-methyl acetate,
tricyclo[5.2.1.0$^{2,6}$]dec-4-yl-methyl and tricyclo[5.2.1.0$^{2,6}$]dec-5-yl-methyl propionate, and
tricyclo[5.2.1.0$^{2,6}$]dec-4-yl-methyl and tricyclo[5.2.1.0$^{2,6}$]dec-5-yl-methyl butyrate.

The specific choice among the compounds of formula (I) depends on production cost factors and on the odour nuances it is desired to achieve. In this respect, among the compounds of formula (I) tricyclo[5.2.1.0$^{2,6}$]decane-methylol and its formate and acetate esters fulfil the said requirement for the most convenient quality/price ratio and, accordingly, they constitute the preferred ingredients according to the invention.

The compounds of formula (I) can be prepared according to conventional techniques by esterifying tricyclo[5.2.1.0$^{2,6}$ decane-methylol, a raw material available from Ruhr Chemie, West Germany ("TCD Alcohol M"), which alcohol can be obtained in accordance with the process described in German Patent No. 934,889.

The following modes of operation illustrate a few examples of the method followed for preparing the ester, respectively ether derivatives, of the invention. The temperatures are indicated in degrees centigrade.

Tricyclo[5.2.1.0$^{2,6}$]dec-4-yl-methyl and
tricyclo[5.2.1.0$^{2,6}$]dec-5-yl-methyl formate 100 g of "TCD Alcohol M" (see above) were cooled to −20° by means of an external cooling device using solid carbon dioxide and acetone. At this temperature, 100 g of mixed formic-acetic anhydride were added dropwise under vigorous stirring within 15 minutes, whereupon the reaction mixture was left at 0° during 3 hrs and at 25° for 15 hrs. After diluting it with 200 ml of ether, the said mixture was washed with two fractions of 100 ml each of water and two fractions of an equal volume of 15% sodium carbonate aqueous solution. The usual working up of the ethereal phase followed by fractional distillation of the obtained residue gave 100 ml of the desired formate having b.p. 47°–49°/0.1 Torr.
IR: 1730, 1465, 1170 and 925 cm$^{-1}$;
NMR(CCl$_4$): 3.85 (2H,d,j= 14 cps); 7.9 (1H,s) δ ppm The alcohol used as starting material in the preparation described above occurred in the form of a mixture of positional isomers. Moreover, owing to the presence of several chirality centres in its molecule, the said alcohol may occur in the form of a diastereoisomeric mixture and, consequently, tricyclo[5.3.1.0$^{2,6}$]decane-methylol is better illustrated by the following formula

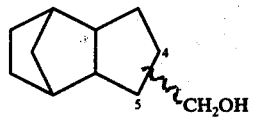

It has to be appreciated by those skilled in the art that, by way of consequence, the ester and ether derivatives of formula (I) can also occur in the form of isomeric mixtures. Said mixtures are perfectly suitable for most of the practical utilizations considered in the field of perfumery and defined in the present invention; accordingly, a further isolation and/or purification of the individual compounds of the defined mixture is superfluous and not economically sound.

Tricyclo [5.2.1.0$^{2,6}$]dec-4-yl-methyl and
tricyclo[5.2.1.0$^{2,6}$]dec-5-yl-methyl acetate 100 g of "TCD Alcohol M" were mixed with 100 g of acetic anhydride in the presence of 10 g of potassium carbonate and the mixture obtained was kept under stirring during 3 hrs at 100°. After cooling, the reaction mixture was diluted with 200 ml of ether and filtered and the organic extracts, after usual washing and neutralization, were evaporated to give a residue which, upon distillation, yielded 100 g of the desired acetate having b.p. 57°–58°/0.1 Torr.
IR (neat): 1740, 1385, 1365 and 1030 cm$^{-1}$;
NMR(CCl$_4$): 1.95 (3H,s); 3.7 (2H,d,badly resolved) δ ppm By operating in a way analogous to the process described above, there was obtained the corresponding isobutyrate ester whose analytical characters were as follows:
b.p. 78°–80°/0.1 Torr
IR (neat): 1730, 1465, 1450 and 752 cm$^{-1}$;
NMR(CCl$_4$): 1.15 (6H,d,J= 13 cps); 3.75 (2H,d,J= 14 cps) δ ppm.

Tricyclo[5.2.1.0$^{2,6}$]decylmethylmethyl ether 5 g of "TCD Alcohol M" were mixed with 0.780 g of sodium hydride and 4.65 g of methyl iodide and the whole was kept under stirring at 25° during 20 hrs.

After evaporation of the volatile components, dilution with 5 ml of water and extraction with two fractions of 50 ml each of ether, the usual workup gave a residue which, upon distillation, yielded 4 g of the desired ether having b.p. 36°–38°/0.1 Torr.
IR (neat): 1475, 1455, 1380 and 955 cm$^{-1}$;
NMR(CCl$_4$): 3.2 (3H,s) δ ppm.

By operating in much the same way as that indicated above and replacing methyl iodide by allyl bromide, there was obtained tricyclo[5.2.1.0$^{2,6}$]decylmethyl allyl ether having b.p. 50°–52°/0.1 Torr.
IR (neat): 3080, 1645, 1342 and 917 cm$^{-1}$;
NMR(CCl$_4$): 3.0-3.4 (2H,badly resolved); 3.75-3.95 (2H, badly resolved); 4.9–6.2 (3H) δ ppm.

The invention is illustrated by the following examples. It has to be understood, however, that these examples are not limitative and the invention is not to be considered as restricted thereto.

EXAMPLE 1

Perfume composition
A base perfume composition of "lavender" type fragrance destined to be incorporated into toilet soaps was prepared by mixing together the following ingredients (parts by weight):

| | |
|---|---|
| Lavandin oil | 250 |
| Linalyl acetate | 100 |
| Linalol | 100 |
| trans-Epoxyocimene 10%*[1] | 100 |
| Diisobutylcarbinyl acetate | 60 |
| Geraniol | 50 |
| Coumarin | 40 |
| Cedar wood oil | 30 |
| Terpineol | 30 |
| β-Damascone 10%*[2] | 20 |
| Trimethylcyclohexenyl-carbaldehyde 10%* | 10 |
| 1-(3,3-Dimethyl-cyclohex-6-en-1-yl)-pent-4-en-1-one 1%*[3] | 10 |
| Total | 800 |

*in diethyl phthalate
[1]Myroxide, source : Firmenich SA, Geneva, Switzerland, U.S. Pat. No. 3,979,425
[2]β-Dorinone ®, source : Firmenich SA, U.S. Pat. No. 3,928,456
[3]Neogal, source : Firmenich SA, British Pat. No. 1,435,887

By adding to 80 g of the above base composition 20 g of tricyclo[5.2.1.0$^{2,6}$]decylmethyl acetate, obtained according to the procedure described above, there was obtained a novel composition which possessed an enhanced lavender scent, the character of which was more natural and elegant than that of the base composition.

EXAMPLE 2

A base perfume composition of "rhubarb" type fragrance was prepared by admixing the following ingredients (parts by weight):

| | |
|---|---|
| 4-Methyl-4-phenyl-2-pentyl acetate | 150 |
| Cariophyllene formate[4] | 100 |
| Terpineol | 100 |
| 3,3,5-Trimethylhexyl acetate | 100 |
| Styrallyl acetate | 100 |
| Phenylethanol | 80 |
| Cyclosia Base ®[5] | 50 |
| Methyl-dihydrojasmonate[6] | 40 |
| Lavender oil | 20 |
| α-iso-Methylionone | 10 |
| Total | 750 |

[4]Mixture of 4,4,8-trimethyl-tricyclo[6.3.1.0$^{2,5}$]dodec-1-yl and 4,4,8-trimethyl-tricyclo[6.3.1.0$^{1,5}$]dodec-2-yl formate, U.S. Pat. No. 3,978,008.
[5)6)]source: Firmenich SA.

By adding to 75 g of the above base composition 25 g of tricyclo[5.2.1.0$^{2,6}$]decyl-methyl acetate, obtained as described above, there was obtained a novel composition possessing a rounder fragrance than the base composition. Its character was, moreover, more acidulous and reminiscent of natural rhubarb.

EXAMPLE 3

A base perfume composition of woody fragrance character was prepared by mixing the following ingredients (parts by weight):

| | |
|---|---|
| p-ter-Butylcyclohexylacetate | 200 |
| Cedar wood oil of Florida | 100 |
| 1-(3,3-Dimethyl-cyclohex-6-en-1-yl)-pent-4-ene-1-one 1%*[3] | 80 |
| Galbanum resinoid | 60 |
| Galbanolene 1%*[7] | 20 |
| Coumarin | 20 |
| Linalol | 20 |
| Styrallyl acetate | 20 |
| Isobornyl acetate | 20 |
| Linalyl acetate | 40 |
| 4-Isopropyl-cyclohexymethanol[8] | 10 |
| Labdanum resinoid | 10 |
| Total | 600 |

*in diethyl phthalate
[3]see footnote[3] of Example 1
[7]U.S. Pat. No. 3,960,977
[8]see footnote[4] of Example 2

The obtained perfume base possesses a well-defined woody character. The addition thereto of 60 parts by weight of tricyclo[5.2.1.0$^{2,6}$]decylmethyl acetate conferred to the said base more elegance and helped to develop a rhubarb-type character which perfectly matched the woody scent.

EXAMPLE 4

A base composition destined to be incorporated into toilet soaps was prepared as indicated in above Example 3. To the thus obtained base there were added 20 parts by weight of tricyclo[5.2.1.0$^{2,6}$]decylmethyl formate to yield a novel composition, the woody note of which was more marked. It possessed, moreover, an iris character.

EXAMPLE 5

A base perfume composition was prepared by admixing the following ingredients (parts by weight):

| | |
|---|---|
| Phenylethanol | 300 |
| Tricyclo[5.2.1.0$^{2,6}$]decane-methylol | 200 |
| Heptylacetate | 80 |
| p-ter-Butylcyclohexylacetate | 80 |
| Dimethyloctanol | 60 |
| Benzyl salicylate | 50 |
| 1-(3,3-Dimethyl-cyclohex-6-en-1-yl)-pent-4-en-1-one 1%[3] | 50 |
| Diisobutylcarbinol | 40 |
| 4-Isopropyl-cyclohexymethanol[8] | 40 |
| Dimethylhydroquinone | 20 |
| Geranonitrile 10%* | 80 |
| Total | 1000 |

*in diethyl phthalate
[3)and 8)]see Examples 1 and 3, respectively

Tricyclo[5.2.1.0$^{2,6}$]decane-methylol confers to the flowery composition given above a Ylang-Ylang character. The obtained composition is particularly useful for perfuming washing powders.

In isolated form, the above-mentioned tricyclo[5.2.1.0$^{2,6}$]decane-methylol possesses a powerful scent having a flowery, fresh character, whereas the corresponding acetate develops a pleasant woody, green smell reminiscent of certain nuances of rhubarb and the corresponding formate develops a woody note with an iris-like character.

What is claimed is:

1. A process for preparing perfume compositions comprising the step of admixing a fragrance-imparting amount of a compound of formula

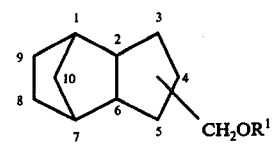

(I)

wherein:
symbol $R^1$ represents a lower saturated or unsaturated linear or branched alkyl radical, having from 1 to 6 carbon atoms, an acyl radical containing from 1 to 6 carbon atoms or a hydrogen atom, and the side-chain is bound to cyclopentane ring at positions 4 or 5 of the said ring;
to confer a flowery, fruity or woody note to such perfume compositions.

2. A perfume composition comprising a fragrance-modifying amount of a compound of formula (I) as set forth in claim 1.

3. A process according to claim 1 wherein the fragrance-imparting compound is admixed in an amount less than about 50% by weight.

4. A perfume composition according to claim 2 wherein the fragrance-modifying compound is present in an amount less than about 50% by weight based on the total weight of the composition.

5. A perfume composition according to claim 2 wherein the fragrance-modifying compound (I) is present in an amount between about 0.5 and 5% by weight based on the total weight of the composition.

6. A perfume composition according to claim 2 wherein $R^1$ represents a formyl radical.

7. A perfume composition according to claim 2 wherein $R^1$ represents an acetyl radical.

8. A perfume composition according to claim 2 wherein $R^1$ represents hydrogen.

* * * * *